United States Patent [19]
Amselem

[11] 3,957,995
[45] May 18, 1976

[54] PHARMACEUTICAL COMPOSITION COMPRISING VINCAMINE AND THEOPHYLLINE

[75] Inventor: Armand Amselem, Toulouse, France

[73] Assignee: Parcor, Paris, France

[22] Filed: Dec. 23, 1974

[21] Appl. No.: 536,942

[30] Foreign Application Priority Data
Dec. 28, 1973 France................................ 73.46741

[52] U.S. Cl................................ 424/253; 424/254; 424/262
[51] Int. Cl.$^2$.............. A61K 31/475; A61K 31/515; A61K 31/52
[58] Field of Search............ 424/253, 258, 254, 262

[56] References Cited
OTHER PUBLICATIONS

Forschag — Chem. Abst., Vol. 78, (1973), p. 62167d.
Kisfaludy et al., Chem. Abst., Vol. 73, (1970), p. 35598k.
U.S. Dispensatory — 25th Edition, (1955), p. 1411.

*Primary Examiner*—Sam Rosen
*Attorney, Agent, or Firm*—Cushman, Darby & Cushman

[57] ABSTRACT

The herein disclosed invention is directed to pharmaceutical compositions of vincamine and theophylline having cerebral vasodilator activity.

14 Claims, No Drawings

PHARMACEUTICAL COMPOSITION COMPRISING VINCAMINE AND THEOPHYLLINE

The present invention relates to pharmaceutical compositions and particularly to compositions having cerebral vasodilator activity.

In one aspect, the invention provides a pharmaceutical composition comprising vincamine or a non-toxic salt thereof and theophylline or a non-toxic salt or derivative thereof.

Vincamine, which was discovered by E. S. Zabolotnaja in 1950, is the main alkaloid of the small periwinkle: vinca minor (Apocynaceae). It has the empirical formula $C_{21}H_{26}O_3N_2$ and the following structural formula:

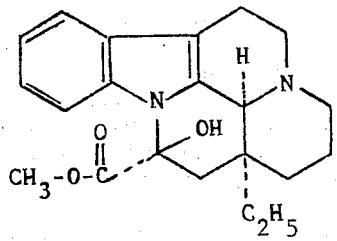

Its synthesis is described by Kuehne in J. Am. Chem. Soc. 86, 2946 (1964).

Numerous publications have noted the many interesting physiological properties of this alkaloid, which is a cerebral vasodilator and oxygenator, with a slight hypotensive and sedative activity.

The composition of the invention may contain, instead of basic vincamine, a non-toxic addition salt thereof with a mineral or organic acid and/or a quaternary ammonium derivative thereof.

We have found in our tests that the vasodilator activity of vincamine is potentiated by theophylline, which may be present in the form of a non-toxic salt or active derivative thereof, e.g. a derivative having the same general activity as theophylline itself. Examples of suitable derivatives are aminophylline (hydrated theophylline ethylenediamine, described on pp 94–96 of the French Pharmacopoeia [8th edition]), neutraphylline (dihydroxypropyl theophylline) and etaphylline (diethylene-diamine theophylline ethanoate).

The tests carried out show that in the presence of theophylline the cerebral vasodilator effect of vincamine is increased and that the combination of vincamine and theophylline produces effects which are clearly greater than those produced by the simple addition of the effects brought about by vincamine and theophylline.

Generally, vincamine and theophylline are combined in a ratio, by weight of vincamine (expressed as a free base) to theophylline, of 0.01 to 0.1 and preferably 0.25 to 0.75.

It is also advantageous to mix the two main constituents of the combination with a barbiturate of the phenobarbital type.

This barbituate is used in a ratio by weight of the barbiturate, expressed as phenobarbital, to theophylline, of about 2 to 0.02, preferably from 1 to 0.1.

The barbiturate of the type phenobarbital when present, completes and prolongs the action of theophylline and vincamine. On account of its sedative properties, it normalises the neuropsychic condition which is often disturbed in patients suffering from cerebral circulatory deficiency.

The results of tests carried out on the compositions of the invention are reported hereinafter:

I TOXICOLOGICAL STUDY

The study related to:

acute toxicity
chronic toxicity
delayed toxicity
local and general tolerance and allowed us to confirm that the composition of the invention is perfectly tolerated when administered by the oral, parenteral or rectal route, without causing any local or general reaction whatsoever. It is not an irritant, and has the advantage of excellent tolerance.

II PHARMACOLOGICAL STUDY

This related to the cerebral vasodilator action of vincamine, theophylline, and the combination of the invention.

The experiments were performed on dogs; they demonstrated the clear potentiation of the cerebral vasodilator and spasmolytic action of vincamine in the presence of theophylline. This potentiation results in an effect which is clearly superior to the sum of the effects produced by theophylline and vincamine when used alone.

The different products to be tested were administered per os: different dogs thus received 30 mg/kg of vincamine (group A), 100 mg/kg of theophylline (group B) and the combination according to the invention (group C) containing 30 mg/kg of vincamine and 100 mg/kg of theophylline.

The rheographic study allows one to determine for the different groups the blood flow in the vertebral artery, the main supply route to the brain, which is proportional to the degree of vasodilation achieved, and the blood pressure in the internal maxillary vein, which is the return route for cerebral blood.

The results are given in the following table, which indicates the average percentage increase for each group, as against the untreated control animal, in the blood flow in the vertebral artery and the blood flow in the internal maxillary vein.

|  | Blood flow in the vertebral artery (% increase) | Blood pressure in the internal maxillary vein (% increase) |
|---|---|---|
| Group A 30 mg/kg vincamine | 37 | 41 |
| Group B 100 mg/kg theophylline | 15 | 14 |
| Group C 30 mg/kg vincamine and 100 mg/kg of thiophylline | 68 | 71 |

The sedative action of the barbiturate was studied in the mouse; the combination of the invention containing 30 mg/kg of vincamine and 100 mg/kg of theophylline was administered by oral route to 2 groups of animals (A and B). Group B is also given, by oral route, 10 mg/kg of phenobarbital. After 20 minutes, it is seen that whereas the behaviour of the animals in group A is unchanged, 65% of the animals in group B are asleep and the remaining mice have a very reduced motor activity.

This remarkable synergistic action on the cerebral blood flow indicates that the combination of the invention may be used to advantage in human and veterinary medicine.

In the compositions to the invention, the active principles are generally combined with a therapeutically administrable carrier or excipient. Thus, the compositions may advantageously be formulated for oral administration in the form of tablets, coated tablets, capsules and drops. They may also be formulated for parenteral administration in the form of an injectable solution, and for rectal administration in the form of suppositories.

The compositions may be formulated in dosage unit form, each single dose advantageously containing from 0.005 to 0.050 g of vincamine, 0.050 to 0.500 g of theophylline and 0.010 to 0.100 g of phenobarbital, while the daily dose may vary from 0.005 to 0.100 g for vincamine, from 0.050 to 1.50 g for theophylline and from 0.010 to 0.300 g for phenolbarbital.

The following examples illustrate the invention.

EXAMPLE 1

COATED TABLETS

|  |  |  |
|---|---|---|
|  | vincamine | 0.015 g |
|  | theophylline | 0.200 g |
|  | phenobarbital | 0.050 g |
| core | rice starch | 0.010 g |
|  | magnesium stearate | 0.010 g |
|  | glucose | 0.020 g |
|  | white shellac | 0.005 g |
|  | gelatin | 0.005 g |
|  | talc | 0.010 g |
| coating | titanium oxide | 0.010 g |
|  | white wax | 0.010 g |
|  | white sugar | q.s.p.1 coated tablet |

EXAMPLE 2

CAPSULES

|  |  |
|---|---|
| vincamine (free base) | 0.010 g |
| theophylline | 0.250 g |
| starch | 0.001 g |
| talc | 0.005 g |
| magnesium stearate | 0.005 g |
| lactose | 0.020 g |

EXAMPLE 3

TABLETS

|  |  |
|---|---|
| vincamine | 0.020 g |
| aminophylline | 0.100 g |
| barbital | 0.100 g |
| starch | 0.005 g |
| silica gel | 0.010 g |
| faecula | 0.010 g |
| gelatin | 0.005 g |
| sodium lauryl sulphate | 0.002 g |
| magnesium stearate | 0.005 g |
| sugar | 0.010 g |
| stearic acid | 0.010 g |

EXAMPLE 4

INJECTABLE SOLUTION

|  |  |
|---|---|
| vincamine | 0.010 g |
| theophylline | 0.100 g |
| isotonic solvent | q.s.p.5 ml |

EXAMPLE 5

SUPPOSITORIES

|  |  |
|---|---|
| vincamine | 0.015 g |
| theophylline | 0.200 g |
| sodium phenobarbital | 0.100 g |
| semi-synthetic triglycerides | q.s.p. 1 suppository |

When used in preventive or curative medicine in cerebral circulatory deficiency, the compositions of this invention can be beneficial in the treatment of patients suffering from neurological disorders of vascular origin.

What we claim is:

1. A pharmaceutical composition comprising 0.005 to 0.50 grams of vincamine and 0.050 to 0.500 grams of theophylline, the weight ratio of vincamine to theophylline being from 0.01 to 0.1:1.

2. Composition as claimed in claim 1, wherein said weight ratio is from 0.025 to 0.075:1.

3. Composition as claimed in claim 1, wherein vincamine is present as a derivative thereof selected from the group consisting of a non-toxic addition salt thereof and a non-toxic quaternary ammonium derivative thereof.

4. Composition as claimed in claim 1, wherein theophylline is present as a derivative thereof selected from the group consisting of theophylline ethylenediamine, dihydroxypropyl theophylline and diethylene-diamine theophylline ethanoate.

5. Composition as claimed in claim 2, wherein vincamine is present as a derivative thereof selected from the group consisting of a non-toxic addition salt thereof and a non-toxic quaternary ammonium derivative thereof.

6. Composition as claimed in claim 3, wherein theophylline is present as a derivative thereof selected from the group consisting of theophylline and diethylene-diamine theophylline ethanoate.

7. Composition as claimed in claim 1, which comprises 0.010 to 0.100 grams of phenobarbital, the weight ratio of phenobarbital to theophylline being 2 to 0.02:1.

8. Composition as claimed in claim 7, wherein said weight ratio of the phenobarbital to theophylline is 0.1:1.

9. Composition as claimed in claim 1 in the form of tablets.

10. Composition as claimed in claim 1 in the form of capsules.

11. Composition as claimed in claim 1 in the form of suppository.

12. A process for treating a patient who suffers from cerebral circulatory deficiency, which comprises administering daily to said patient from 0.005 to 0.100 g vincamine together with from 0.05 to 1.50 g theophylline, the weight ratio of vincamine to theophylline being from 0.01 to 0.1:1.

13. A process as claimed in claim 12, which comprises administering daily to said patient from 0.010 to 0.300 g phenobarbital together with said vincamine and theophylline, the weight ratio of phenobarbital to theophylline being 2 to 0.02:1.

14. Process as claimed in claim 13, which comprises administering said vincamine, theophylline and phenobarbital as dosage unit forms, each form comprising from 0.005 to 0.050 g vincamine, from 0.050 to 0.500 g theophylline and from 0.010 to 0.100 g phenobarbital.

* * * * *